(12) United States Patent
Tanaka et al.

(10) Patent No.: US 7,162,527 B2
(45) Date of Patent: Jan. 9, 2007

(54) INFORMATION COMMUNICATING SYSTEM, INFORMATION TRANSMITTING APPARATUS AND INFORMATION TRANSMITTING METHOD

(75) Inventors: Kiko Tanaka, Tokyo (JP); Yasushi Odaira, Tokyo (JP)

(73) Assignee: CMIC Co., Ltd., Tokyo (JP)

( * ) Notice: Subject to any disclaimer, the term of this patent is extended or adjusted under 35 U.S.C. 154(b) by 773 days.

(21) Appl. No.: 10/194,299

(22) Filed: Jul. 15, 2002

(65) Prior Publication Data
US 2004/0010604 A1    Jan. 15, 2004

(51) Int. Cl.
*G06F 15/16* (2006.01)
(52) U.S. Cl. ............... 709/229; 709/203; 709/217; 709/225; 709/226
(58) Field of Classification Search ............... 709/203, 709/217, 219, 225, 226, 229; 707/10
See application file for complete search history.

(56) References Cited
U.S. PATENT DOCUMENTS
5,933,829 A * 8/1999 Durst et al. ............... 707/10

6,865,608 B1 * 3/2005 Hunter ....................... 709/229

FOREIGN PATENT DOCUMENTS

| JP | 06-236386 | 8/1994 |
|---|---|---|
| JP | 06-309557 | 11/1994 |
| JP | 10-171758 | 6/1998 |
| JP | 2002-189805 | 7/2002 |

\* cited by examiner

*Primary Examiner*—Yves Dalencourt
(74) *Attorney, Agent, or Firm*—Finnegan, Henderson, Farabow, Garrett, & Dunner, L.L.P.

(57) ABSTRACT

An information transmitting apparatus is connected to a reading device to read readable codes from an input sheet. On the input sheet, an input item is provided similar to the input item to be provided in an information input page for Internet communication, and input information to be input into each input item is provided in a readable code, for example, a bar code. When input information is read from the input sheet by the reading device, the information transmitting apparatus transmits the read input information as input information for an information input page, to the information receiving apparatus. Input into the information input page of the Internet communication is made easier.

9 Claims, 10 Drawing Sheets

| NAME OF PHARMACEUTICAL DRUG | CODE | NAME OF PHARMACEUTICAL DRUG | CODE |
|---|---|---|---|
| A | ||||| | · | · |
| B | ||||| | · | · |
| C | ||||| | · | · |
| D | ||||| | · | · |
| · | · | · | · |
| · | · | · | · |
| · | · | · | · |
| · | · | · | · |
| · | · | X | ||||| |
| · | · | Y | ||||| |
| · | · | Z | ||||| |

SELECTIVE INPUT SHEET 72

FIG. 6

INFORMATION COMMUNICATING SYSTEM, INFORMATION TRANSMITTING APPARATUS AND INFORMATION TRANSMITTING METHOD

BACKGROUND OF THE INVENTION

1. Field of the Invention

The present invention generally relates to a system for transmitting information utilizing Internet technology, and more particular to technology to make information input operations easy at the transmitting side.

2. Description of the Related Art

Conventionally, in the field of clinical trials, paper is used for transmission of test data. An investigational site (a hospital) enters the test data in an exclusive entry sheet (a case report form). Then, the entry sheet is sent to a test data administrator by facsimile or mail.

With the Internet becoming increasingly widespread, exploitation of the Internet has been considered in such information transmission. For example, a Web page (information input page) for information input is displayed on terminals of the investigational site instead of conventional entry sheets. Input items are arranged on the information input page. Information is input in each input item by utilizing a keyboard. Compared with the use of a facsimile or mail, information is collected easily.

However, when the Internet is utilized, information must be input on the information input page using the keyboard. This is a troublesome task compared with entry operations into the conventional sheet.

In order to make the entry operation easier, it has been considered to provide multiple choices on the information input page. A user may perform the operation to choose from the multiple choices. However, even if the multiple choice method is used, the operation is still troublesome compared with the use of the entry sheet. Also, when there are a large number of choices, the input operation becomes troublesome.

For example, in the above stated clinical trial, there are many input items of the entry sheet to be filled in. Also, many kinds of information can be input into one item regarding names of pharmaceutical drugs or symptoms. Thus, if the entry sheet is replaced by a Web page, the entry operation of the Web page becomes very troublesome.

As stated above, the operation of inputting information to the Internet is troublesome compared with entry into the entry sheet. Assuming that the input task is performed in the same sense as entry into the entry sheet and if the entry task can be performed more easily than the entry into the entry sheet, the manual operation would be considered much simpler.

Here, the clinical trial is mainly taken as an example in order to explain the background of the invention, but the same can be said for the transmission of other information.

SUMMARY OF THE INVENTION

The present invention has been conceived in view of the above described situation, and its purpose is to provide the technology to facilitate input of information through an input page to the Internet.

The information communicating system of the present invention includes an information receiving apparatus and an information transmitting apparatus connected to the information receiving apparatus. The information transmitting apparatus is connected to a reading device which reads readable code from an input sheet, and the input sheet has input item to be created on an information input page for Internet communication as well as input information in a readable code to be input to the input items, and the information transmitting apparatus transmits the input information read from the input sheet by the reading device to the information receiving apparatus, as input information for the information input page.

Preferably, the input sheet has an access code in readable code necessary to access the information receiving apparatus from the information transmitting apparatus, and the information transmitting apparatus accesses the information receiving apparatus by transmitting to the information receiving apparatus the access code obtained from the input sheet by the reading device.

Preferably, the access code is an access code with a term limit on which a prescribed valid term is established, and access to the information receiving apparatus is permitted when the information transmitting apparatus transmits the access code with the term limit read from the input sheet to the information receiving apparatus within the valid term.

Preferably, an input time limit of the access code is set according to time necessary to input the access code by using the reading device, and is shorter than the minimum input possible time to input the access code by keyboard, and when the access code is input within the input time limit, the access to the information receiving apparatus is permitted.

Preferably, a numerical figure input area, in which readable codes are arranged to be used for input of numerical figures, is provided on the input sheet, and the readable codes corresponding to numerical figures are arranged in matrix form in the numerical figure input area.

Preferably, readable codes corresponding to numerical figures are multi dimension codes.

Preferably, the input sheet has plural input area having different input items, and plural area specify readable codes respectively corresponding to the plural input areas, and the transmission reception apparatus accepts input information corresponding to the area specify readable code read by the reading device.

The present invention is not limited to the above aspect of the information communicating system. Other aspects of the present invention are, for example, an information transmitting apparatus, information receiving apparatus, information communicating method, transmitting method, receiving method, and media recording program to cause a computer to execute such method. Also, another aspect of the present invention is the input sheet to be utilized for input into the information input page. A further aspect of the present invention is an access permission device.

BRIEF DESCRIPTION OF THE DRAWINGS

FIG. 6 shows the choice input sheet used in the information input process in FIG. 5.

DESCRIPTION OF PREFERRED EMBODIMENTS

The invention is hereafter explained through a preferred embodiment by making reference to drawings.

In the present embodiment, the invention is used in the transmission of clinical data. However, the invention is not limited to such uses, and can be applied to other optional communication transmission systems.

Figure 1:
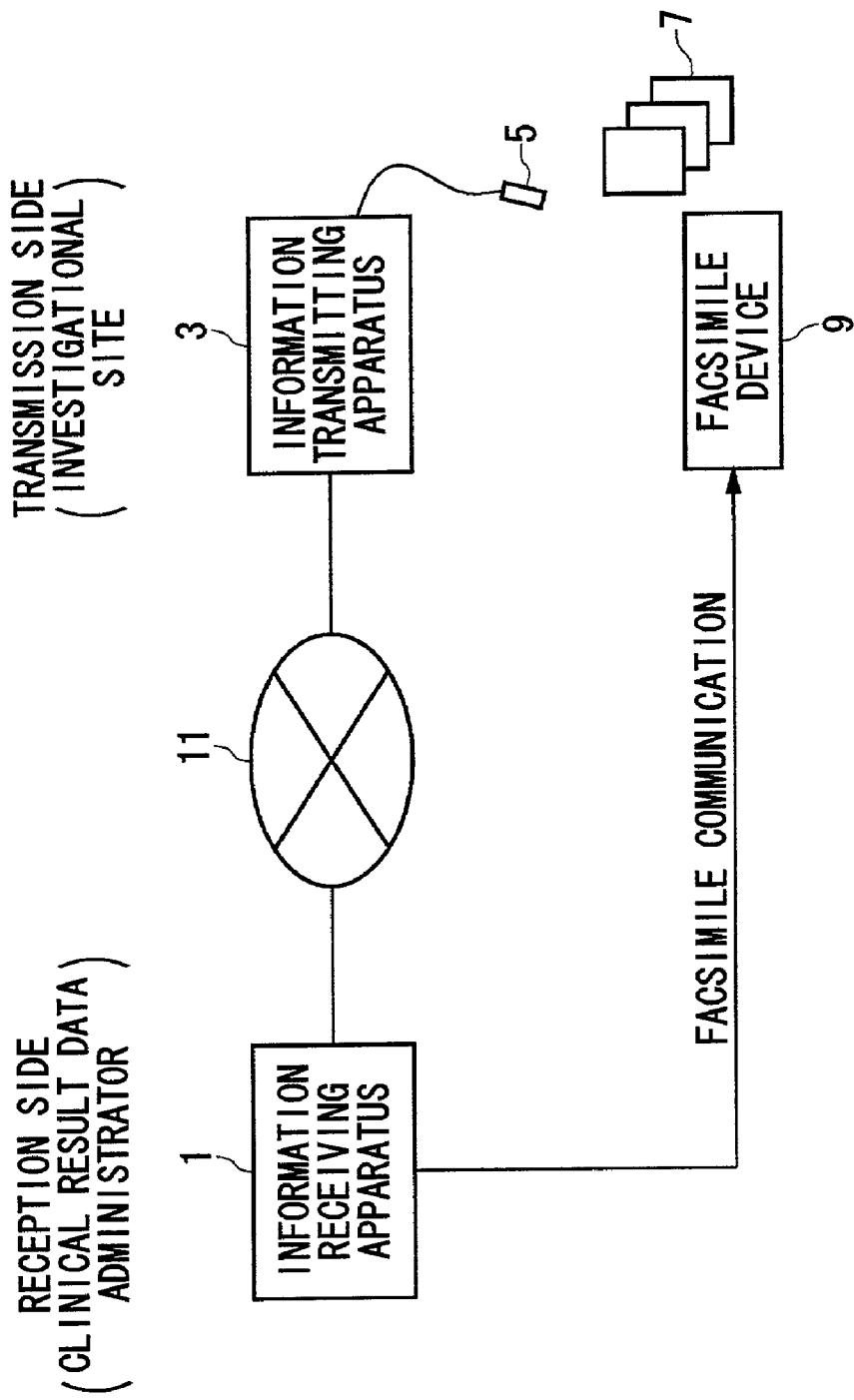
FIG. 1 shows the information communicating system of the embodiment of the present invention.

FIG. 1 shows the information communicating system of the present embodiment. An information receiving apparatus 1 is provided at a clinical result data administrator of the reception side, and an information transmitting apparatus 3 is provided at an investigational site (a hospital) of the transmission side. The information receiving apparatus 1 and the information transmitting apparatus 3 are connected through the Internet 11.

The information transmitting apparatus 3 has a pen type bar code reader 5 and an attached input sheet 7. The bar code reader 5 is one type of reading devices of the present invention, connected to the information transmitting apparatus 3. The input sheet 7 is provided separately from the information transmitting apparatus 3. The input sheet 7 is transmitted from the information receiving apparatus 1 by facsimile transmission and received by the facsimile device 9 of the reception side. Bar codes used for input of clinical trial results are printed on the input sheet 7. The bar code is one type of readable code of the present invention.

When the bar code reader 5 reads the bar code of the input sheet 7, the information (input information) of the clinical trial results is input into the information transmitting apparatus 3. Then, the input information is transmitted from the information transmitting apparatus 3 to the information receiving apparatus 1 through the Internet 11.

Figure 2:
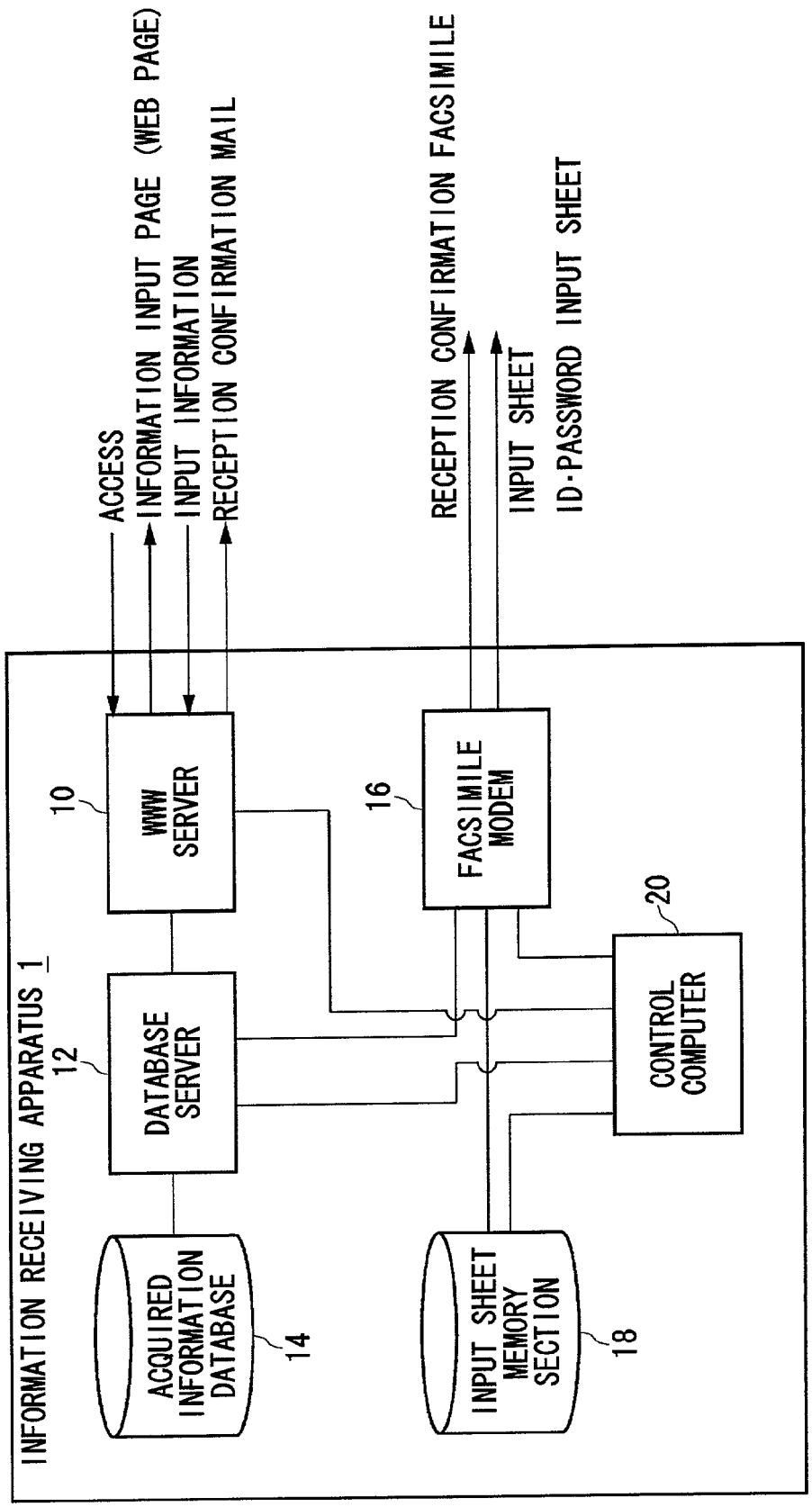
FIG. 2 shows the structure of the information receiving apparatus in FIG. 1.

FIG. 2 shows the structure of the information receiving apparatus 1. The information receiving apparatus 1 has a WWW server 10, database server 12, acquired information database 14, facsimile modem 16, input sheet memory section 18 and control computer 20.

The WWW server 10 transmits the information input page in the form of a Web page to the information transmitting apparatus 3 in response to access from the information transmitting apparatus 3. When the information (clinical trial results) input in the information input page is transmitted from the information transmitting apparatus 3, the WWW server 10 delivers the input information to the database server 12. The database server 12 stores and manages the information of acquired clinical trial results in the acquired information database 14.

When the database server 12 completes the storing of the acquired information into the acquired information database 14, a confirmation mail is transmitted from the WWW server 10 to the information transmitting apparatus 3, or a confirmation facsimile sheet is transmitted from the facsimile modem 16 to the facsimile device 9 of the investigational site.

Also, the input sheet memory section 18 memorizes the input sheet. The input sheet is read from the input sheet memory section 18, and transmitted to the facsimile device 9 of the investigational site by the facsimile modem 16. The facsimile modem 16 further transmits an ID password input sheet (included in the input sheet) upon an instruction of the control computer 20.

The control computer 20 controls the entire operation of the information receiving apparatus 1. The function of each of above stated structures is controlled by the control computer 20. The function of the control computer 20 may be provided on the WWW server 10 or the database server 12, or distributed among such computers.

Also, in the present invention, the function of the WWW server and the function of furnishing input sheets need not be connected in the information receiving apparatus 1.

Figure 3:
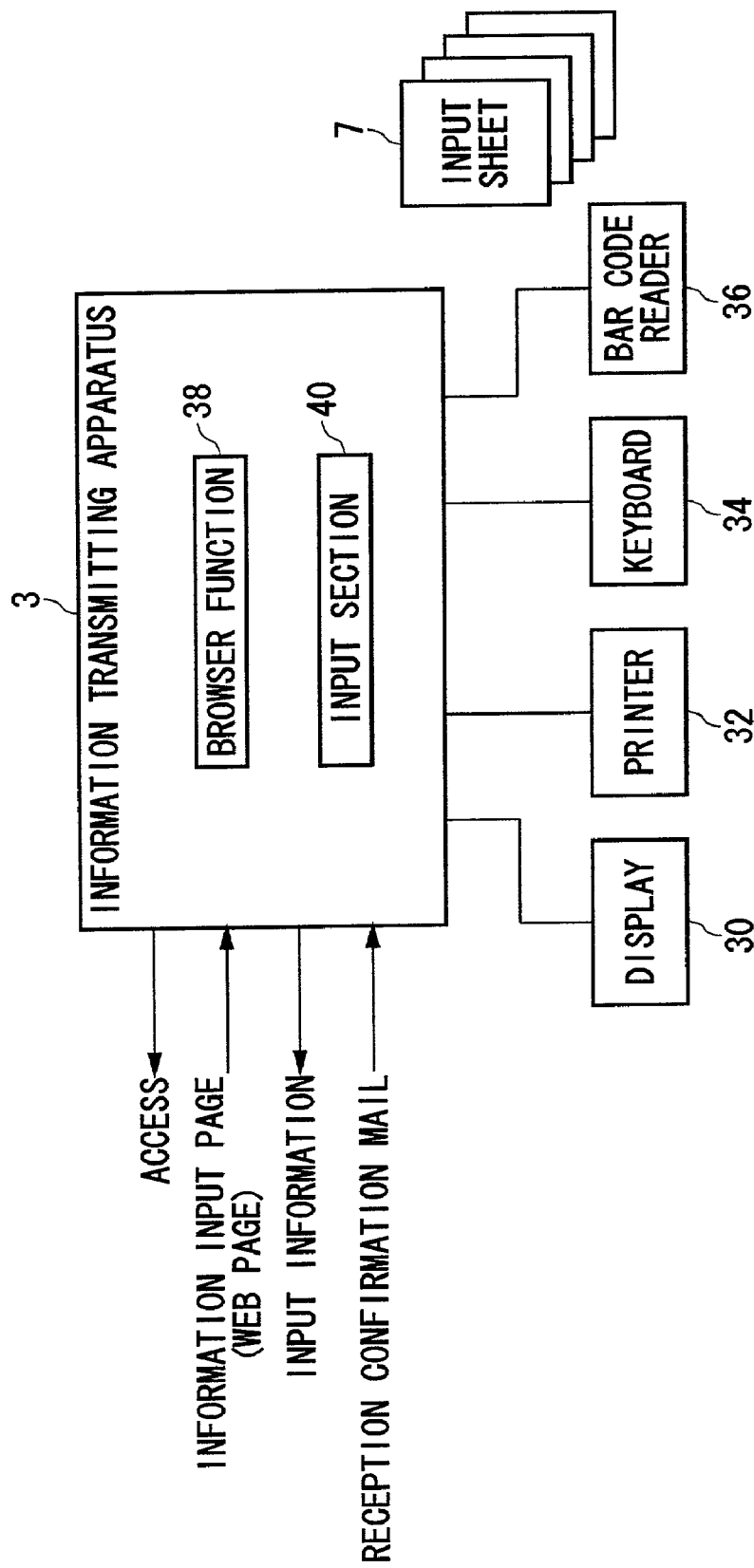
FIG. 3 shows the structure of the information transmitting apparatus in FIG. 1.

FIG. 3 shows the structure of the information transmitting apparatus 3. The information transmitting apparatus 3 is a computer of the investigational site and can be connected to the Internet. The information transmitting apparatus 3 has a display 30 and printer 32 as output devices. Also, the information transmitting apparatus 3 has a keyboard 34, mouse 36 and bar code reader 5, and has the input sheet 7 as an input accessory.

Each input and output device (including the bar code reader) may be connected to the information transmitting apparatus 3 in a wireless manner such as by infrared rays, etc. The input sheet 7 is sent from the information receiving apparatus 1 as stated above through facsimile communication and printed out by the facsimile device (not illustrated). The input sheet 7 may be sent from the information receiving apparatus 1 through the Internet and printed out by the printer 32. The input sheet 7 may be obtained by the investigational site by mail, hand delivery or other means.

The information transmitting apparatus 3 has a browser function 38 and input section 40. The browser function 38 is realized when the information transmitting apparatus 3 executes Internet browser software installed in the information transmitting apparatus 3. The input section 40 processes the information input from the input devices such as the keyboard 34, mouse 36, and bar code reader 5.

Figure 4:
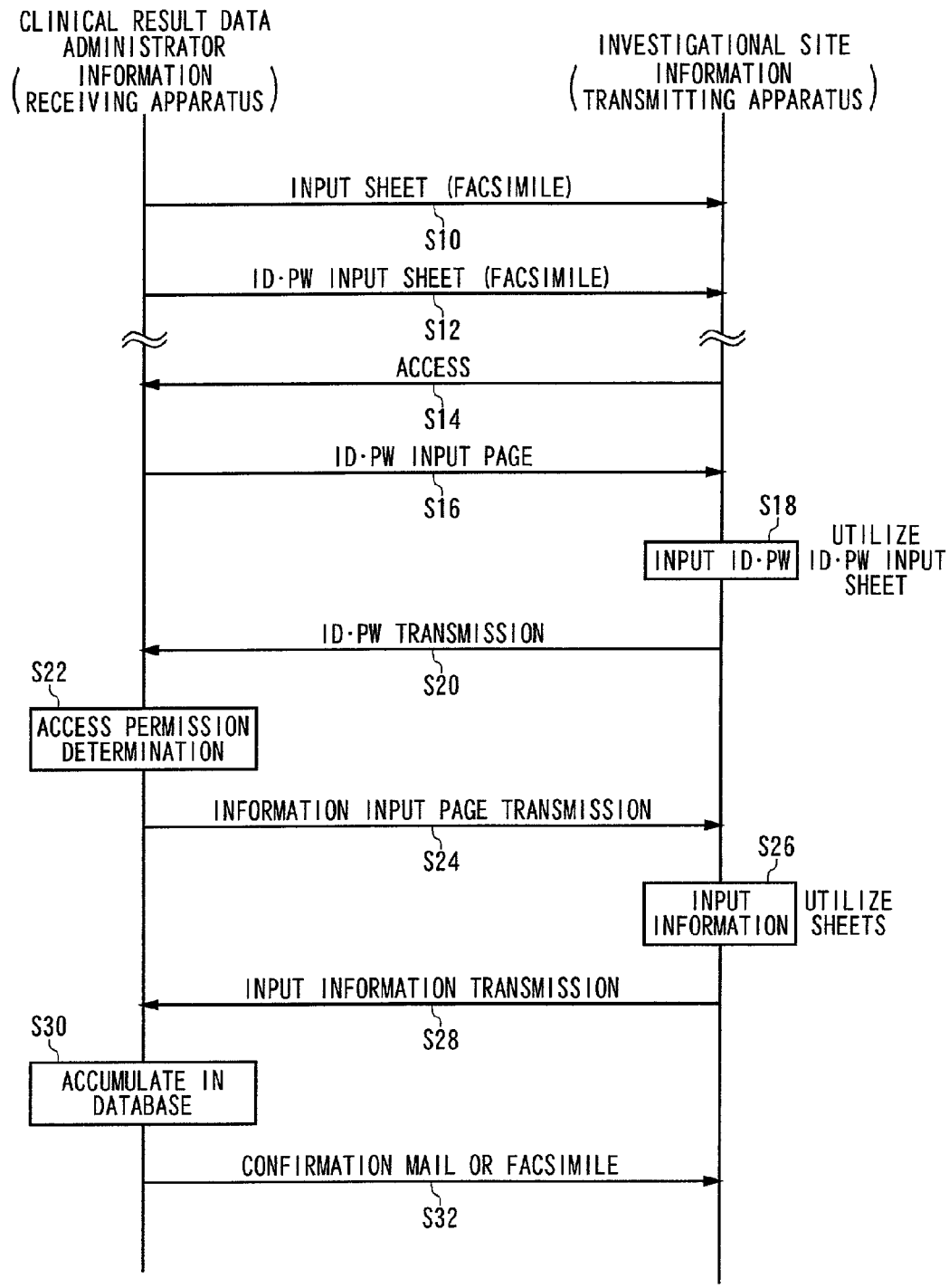
FIG. 4 shows the process of information transmission by the system of FIG. 1.

FIG. 4 shows a process of transmitting the information on clinical trial results from the investigational site (information transmitting apparatus 3) to the clinical result data administrator (information receiving apparatus 1).

Prior to information transmission, first, the input sheet 7 is sent to the investigational site (S10). Further, an ID password input sheet is sent as a part of the input sheet to the investigational site (S12). The ID password input sheet is sent at the time of changing the password (hereafter described).

A user of the investigational site accesses the information receiving apparatus 1 (S14) by operating the information transmitting apparatus 3 at the time of transmitting the clinical trial results information. The information receiving apparatus 1 transmits an ID password input page to the information transmitting apparatus 3 in response to the access (S16). The ID password input page is the Web page, which is one of the information input pages.

At the investigational site, the ID password input page is displayed on the display 30. The user inputs ID and the password using the bar code reader 5 and ID password input sheet (S18). ID and password are transmitted to the information receiving apparatus 1 (S20). After a verification process for verifying ID and password with registered data, permission or denial of access is determined (S22).

Once access is permitted, information input page (Web page) for inputting the clinical trial results is transmitted to the information transmitting apparatus 3 (S24). When the information input page is displayed on the display 30, the user inputs information concerning the clinical trial results using the bar code reader 5 and input sheet 7 (S26). The input information is sent to the information receiving apparatus 1 (S28), and accumulated in the acquired information database 14 (S30). Then, a mail confirming information reception is transmitted to the information transmitting apparatus 3, or a confirmation facsimile sheet is transmitted to the facsimile device 9 of investigational site (S32).

Figure 5:
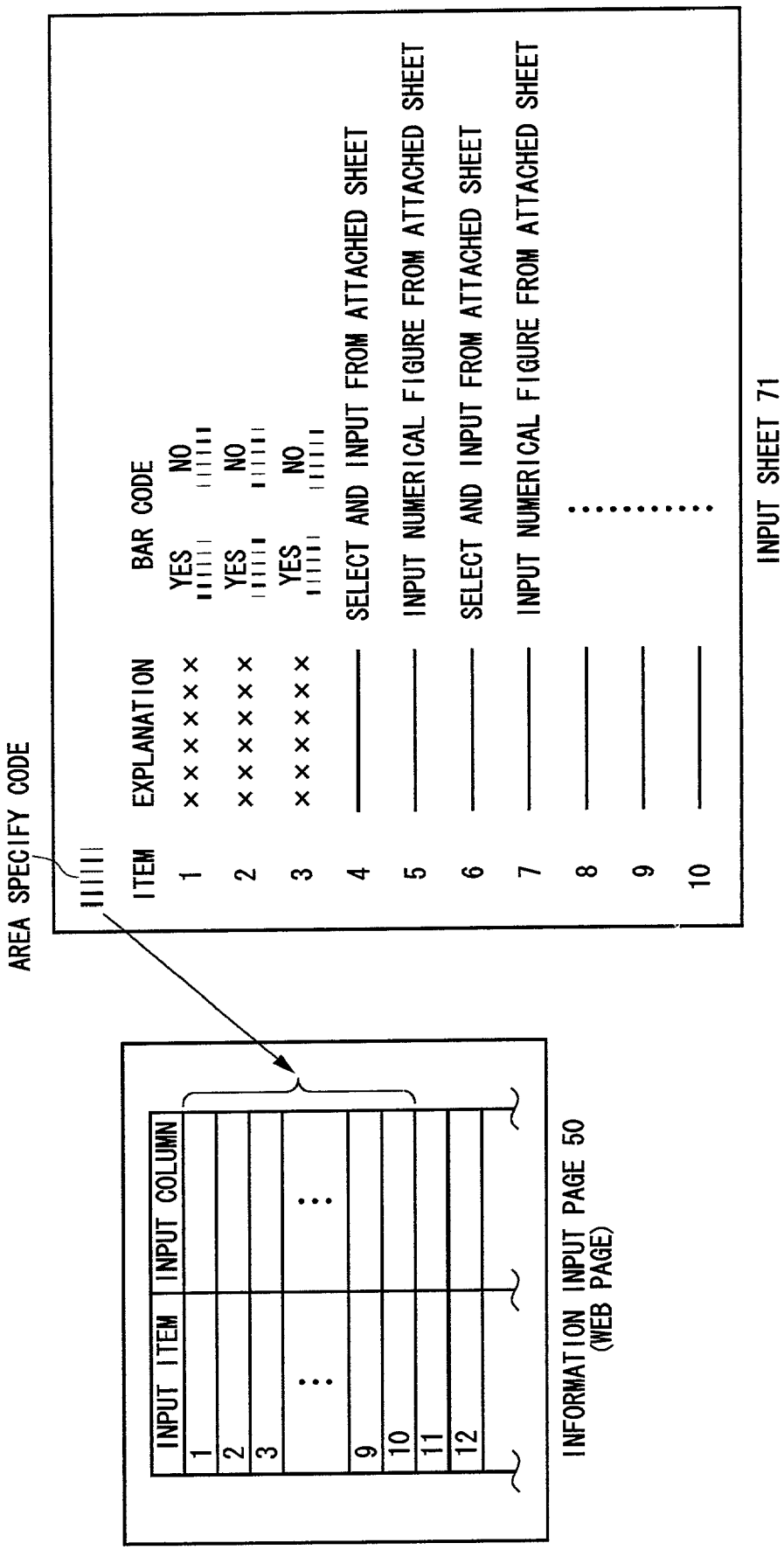
FIG. 5 shows the information input process using the input sheet and the reading device.

FIG. 5 is a drawing for explaining characteristics of the input sheet 7 of the present invention and the input operation using the input sheet 7. FIG. 5 shows the information input page 50 and the input sheet 71 to be used corresponding to the information input page 50. In the present embodiment, a set comprising a plurality of the input sheets is used, but FIG. 5 shows only one of these input sheets. Moreover, a set of a plurality of sheets may be considered as one input sheet, or each sheet may be considered as one of a number of input sheets.

A plurality of input items are arranged on the information input page 50 and input columns are provided corresponding to each item. On the other hand, a plurality of input items are also arranged on the input sheet 71. Input items of the input sheet 71 correspond to the input items of the information input page 50.

The information to be input in each input item is printed in the bar code in the input sheet 71. An answer of "Yes" or "No" is sought in Items 1–3, so bar codes of "Yes" and "No" are printed at a certain place on each item.

Items 4 and 6 require input of names of pharmaceutical drugs. For inputting names of pharmaceutical drugs, a separate input sheet 72 indicated in FIG. 6 is prepared. Names of many pharmaceutical drugs and bar codes corresponding to these pharmaceutical drugs are arranged on this input sheet 72. Names of pharmaceutical drugs are an example of input items having many choices. For other input items, when there are many choices, it is preferable to prepare other similar input sheets.

Figure 7:
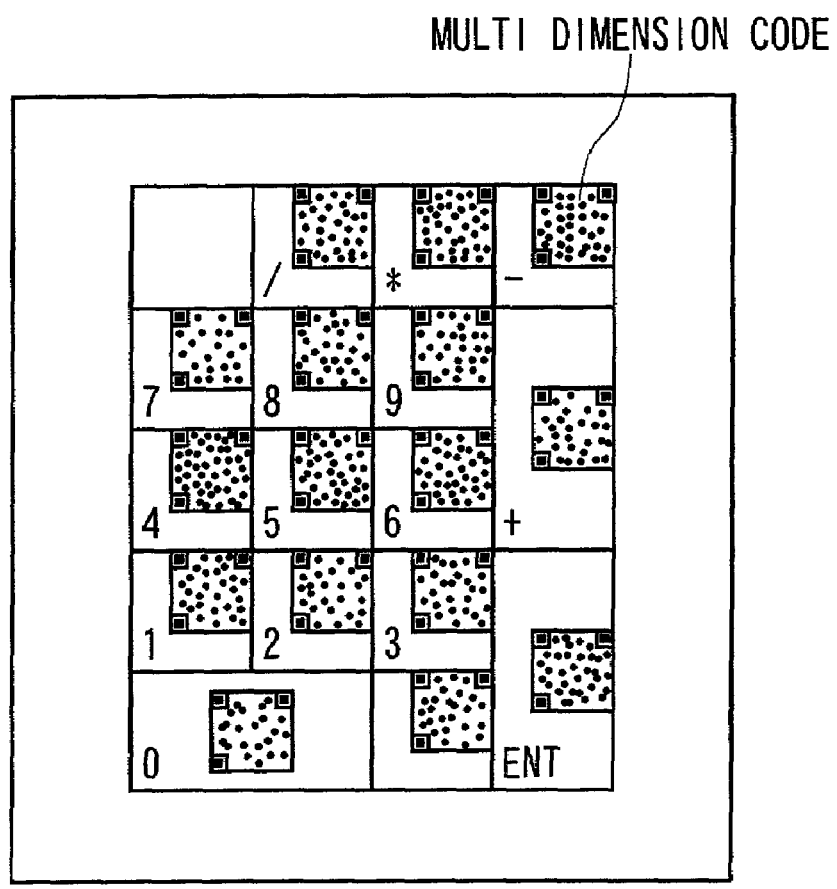
FIG. 7 shows the numerical figure input sheet used in the information input process in FIG. 5.

Items 5 and 7 require input of numerical numbers. For example, a dosage of a pharmaceutical drug. The other input sheet 73 shown in FIG. 7 is prepared for input of numerical numbers. Bar codes of numerical numbers 0–9 and calculation marks are arranged in a matrix on this sheet 73. Here, a multi dimension code, which is explained hereafter, is used. Matrix arrangement of the codes may be similar to key arrangements of a ten-key section of the keyboard.

As shown in FIG. 7, codes of numerical numbers and calculation marks are preferably a multi dimension code. The multi dimension code has a memory density higher than a normal striped pattern bar code, that is, a code with a large volume of information. The multi dimension code relates to the bar code technology and may be considered as a bar code being compressed and changed to the multi dimension (it is sometimes called a second dimension bar code). As the multi dimension code, for example, a stack type code (multilevel method) and a matrix type code are known. If the multi dimension code is used, the length of the code may be shortened and an approximately square code may be used. In doing so, the matrix arrangement of the readable codes can be made approximate to the arrangement of a normal ten-key making the input of numerical figures easy.

Further, in the present embodiment, the normal striped design bar code is used for inputting information other than numerical figures, etc. However, the multi dimension code may appropriately be used for other parts. All of the codes may be the multi dimension code. Alternatively, just some of the codes may be the multi dimension code depending on the conditions on the sheet such as a space, etc.

Also, in each input item of the input sheet 71, an explanation is described regarding the information to be input. This explanation includes the input method and rules such as "select from the attached input sheet". The user may grasp the explanation of the input sheet 71 at the time of input. An explanation is therefore not given on the information input page 50. Design of the information input page 50 may be a simple form of only arranging the input items. Further, at the time of displaying the information input page 50 on the display, the input item and input column may not be displayed, or the input item or input column only may be displayed.

Also, the input sheet comprises a plurality of sheets, and the input sheet 71 in FIG. 5 is one of the plurality of sheets. When one of each sheet is considered as an input area, the input sheet comprises a plurality of areas. Also, as shown by the input sheet 71 of FIG. 5, each sheet is attached with an area specify code to specify the input area (sheet). Further, in the present invention, a plurality of input areas may be arranged on one sheet, or one input area may cover a plurality of sheets.

Input operations using the above stated input sheet are hereafter explained.

Firstly, the user causes the bar code reader to read the area specify code at a corner of the input sheet 71. When, the user touches or approaches the area specify code with the bar code reader, and moves (traces) along the area specify code, the bar code reader 5 reads the area specify code (similar to other bar codes). Moreover, depending on the type of the bar code reader, the bar code reader may only touch or approach the bar code.

The area specify code read by the bar code reader 5 is input into the information transmitting apparatus 3. In response to this, the browser function of the information transmitting apparatus 3 is in a condition of receiving the input information of the input area corresponding to the area specify code. That is, since the input sheet 71 of FIG. 5 is the input area of input items 1–10, when the area specify code is read, the information transmitting apparatus 3 waits for input of items 1–10 of the information input page 50. Further, the information input page is divided into a plurality of input pages, and each information input page may correspond with each input sheet. In this case, the information input page shifts according to reading of the area specify code.

Next, the user inputs the information of the test results to each input item. Here, the user causes the bar code reader 5 to read the input bar code of each input item. The read information (code) is input into the information transmitting apparatus 3, and entered into the column corresponding to the information input page by the browser function.

Regarding items 1–3 of FIG. 5, the user causes the bar code reader 5 to read the code of "YES" or "NO". Regarding items 4, 6, the user selects the code of appropriate pharmaceutical drug from the input sheet 72 of FIG. 6 and causes the bar code reader to read the code. Regarding items 5, 7, the user causes the bar code reader 5 to read the bar code arranged in a matrix on the input sheet 73 of FIG. 7. The user causes the bar code reader to read the bar codes in numerical figures one after another in the same sense as operating the ten-key of keyboard. The code read as above is entered in the input column of the information input page 50.

Moreover, each of bar codes preferably contains codes showing an input column on the corresponding Web page. In doing so, the entry by the browser into the applicable input column is reliably effected. Also, regarding the selective input column and numerical figure input column, the bar code indicating the input column is assigned to each input item. The user causes the bar code reader 5 to read this bar code and then uses the selective input sheet 72 or numerical figure input sheet 73. In doing so, when another input sheets is used, the browser may enter the bar code reliably into an applicable column.

After the input task of one sheet is completed, the input task of the next sheet is similarly performed. When the input task is completed, the user instructs the information transmitting apparatus 3 to transmit the input information of the test results. For example, a transmission button (not illustrated) provided on the information input page is clicked by a mouse. A bar code instructing the transmission may be assigned on the input sheet. When the user causes the bar code reader 5 to read the bar code of transmission instruction, the browser function 5 transmits the input information up to that time upon receiving input of this code.

Figure 8:
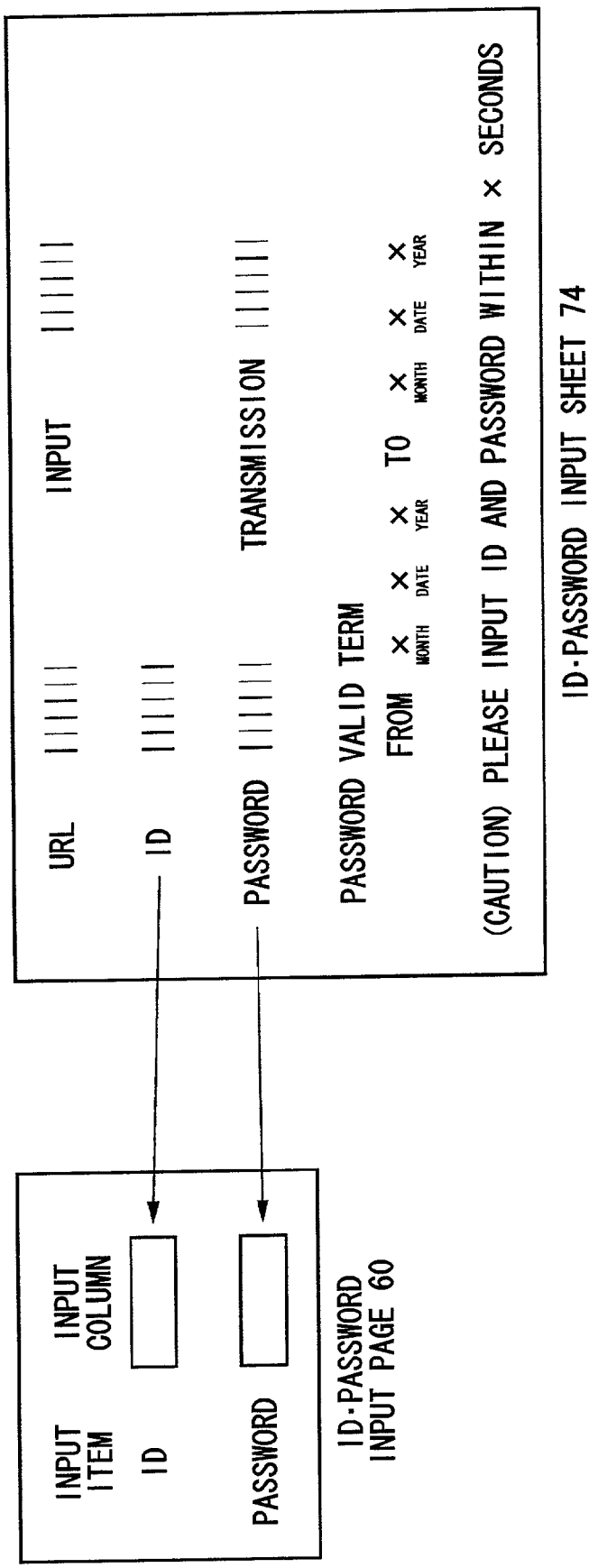
FIG. 8 shows the access process by input of ID and password using the input sheet and reading device.

FIG. 8 shows an ID password input page 60 and an ID password input sheet 74 to be used with it. This sheet is used to access the WWW server of the information receiving apparatus 1 at the time of commencing input and transmission tasks.

An ID and password as input items and their input column is provided on the ID password input page 60. On the other hand, similar input items, that is, ID and password are also provided on the ID password input sheet 74. A bar code of the user's ID and password are also assigned in these items. Further, on the ID password input sheet 74, a bar code corresponding to the URL of WWW server of this system is assigned.

Further, on the ID password input sheet 74, the code to input URL (corresponding to an enter key) and the code for instructing the transmission of the ID and password (corresponding to a transmission instruction button) are arranged. These codes may also be included in the code for the URL and password.

In addition, on the ID password input sheet 74, the valid term of the password and a caution concerning the input time limit of the ID and password is described. These will be explained later.

When accessing the WWW server, the user starts the browser software of the information transmitting apparatus 3. Next, the user causes the bar code reader 5 to read the URL of the ID password input sheet 74, and further causes the bar code reader 5 to read the bar code of input. Upon receiving input of these codes, the information transmitting apparatus 3 accesses the WWW server of the information receiving apparatus 1 through the Internet.

In response to this access, the ID password input page 60 is sent from the information receiving apparatus 1 to the information transmitting apparatus 3, and this page is shown on the display 30. Next, the user causes the bar code reader 5 to read sequentially the ID, password, and transmission instruction code of the ID password input sheet 74. ID and password are sequentially written into the corresponding input columns of ID Password input page 60. Further, in response to input of the transmission instruction code, the ID and password are transmitted to the information receiving apparatus 1. The information receiving apparatus 1 performs verification processing using the ID and password. When the user is specified, the next information input page (FIGS. 5, 50) is sent to the information transmitting apparatus 3.

Next, the access permission device (authentication device) of the present invention is hereafter explained. In the present embodiment, the access permission device is provided on the WWW server of the information receiving apparatus 1 in the form of an access permission function.

Figure 9:
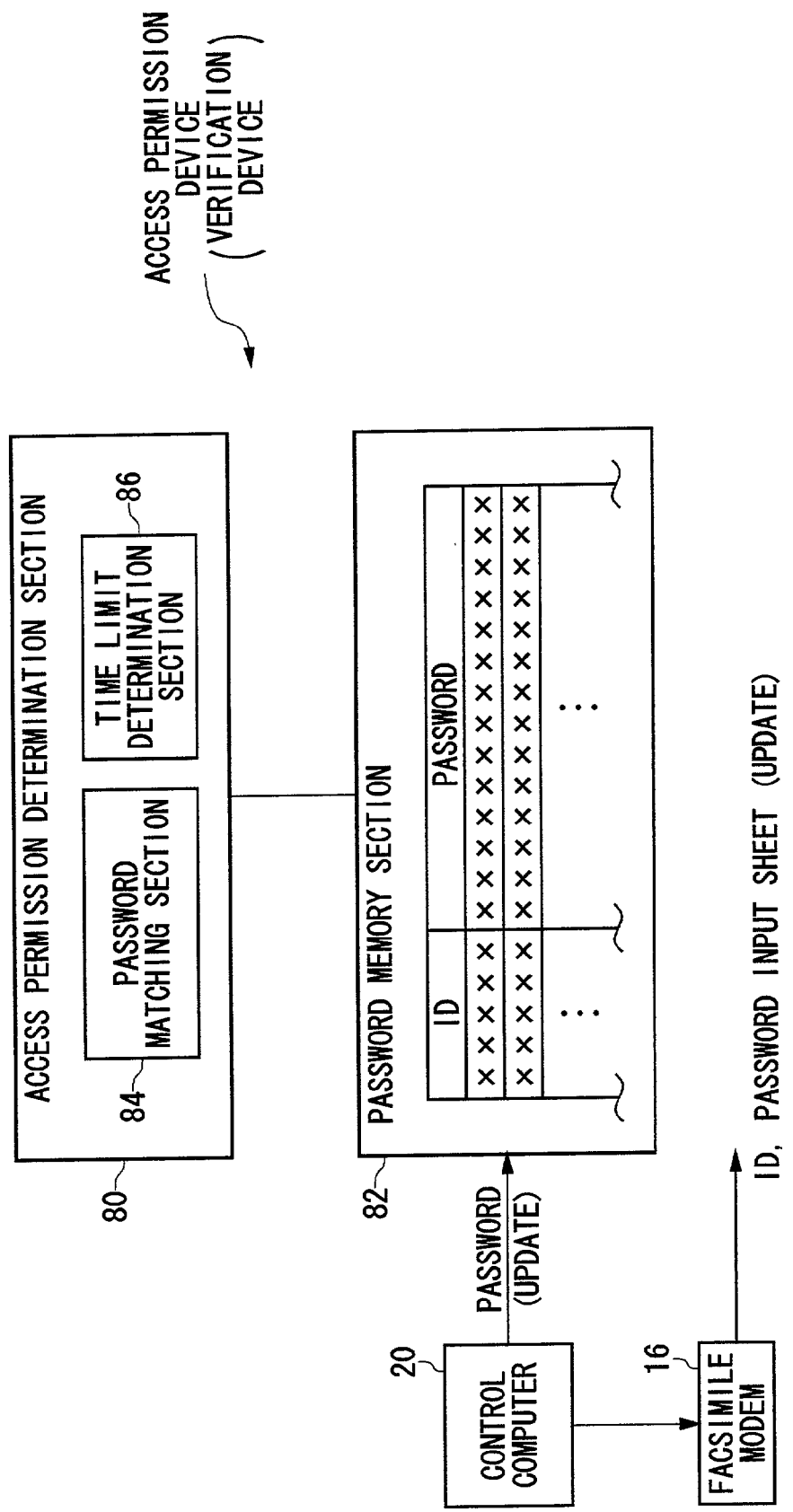
FIG. 9 shows the access permission device incorporated in the system in FIG. 1.

FIG. 9 shows the structure of the access permission device. The access permission device has an access permission determination section 80 and a password memory section 82. The password memory section 82 memorizes the password in connection with the ID of each user as shown in FIG. 9. In the present embodiment, the valid term is established for the password. The password memory section 82 memorizes the password within the valid term.

The valid term of the password is established for a comparatively short appropriate term, for example, one week. The valid term may not be a fixed term. Upon expiration of the valid term, the password is renewed in the following manner.

The password is generated by the control computer 20. The control computer 20 furnishes the password memory section 82 with a new password with a corresponding ID upon expiration of valid term of the present password. The password memory section 82 updates password information with the new password.

The time a new password is generated in the control computer 20 is an appropriate time in advance of the expiration of the valid term of the present password. The control computer 20 produces the data for the ID password input sheet describing the new password and a bar code corresponding thereto. The ID password input sheet describes a valid term of the new password (see FIG. 8). This data is transmitted through the facsimile modem 16 to the facsimile device 9 of the investigational site by facsimile communication. When the valid term of the present password expires, the password input sheet of the investigational site is replaced by a new sheet received by the facsimile.

The access permission determination section 80 has a password matching section 84 and a time limit determination section 86. The password matching section 84 matches the ID and password sent from the information transmitting apparatus 3 of the investigational site. As stated above, the password memory section 82 only memorizes the password within the present valid term. Therefore, the combination of the ID and password obtained matches the combination within the memory section 82, and the use of a proper password within the valid term is determined.

The time limit determination section 86 determines whether or not input of the ID and password at the information transmitting apparatus 3 is carried out within the prescribed input time limit. Here, the input time limit is set based on the time necessary to read the ID and password by the bar code reader 5, and is set for a time shorter than the minimum time required for the possible input time of the ID and password by the keyboard.

The present invention establishes the input time limit in order to prevent illegal access. Generally, the read-out operation using the bar code reader 5 is completed in a short time compared with the operation of inputting the same code using the keyboard. The larger the digit of the ID and password, the larger the time difference between both operations becomes. Therefore, in the present embodiment, the number of digits of the password is set such that both operation times are definitely different, that is, standard operation time of the bar code is much shorter than the minimum input time of the keyboard.

Then, the input time limit is established longer than the standard time necessary to read using the bar code reader 5. Further, the input time limit is set shorter than the minimum time required for input by the keyboard (conversely speaking, in order to make minimum input time of the keyboard longer than the input time limit, the length (digit number) of the ID and password is set).

For example, the total number of digits of the ID and password are set at twenty digits, and the input time limit is set at five seconds.

A caution for the above input time limit is described on the ID password input sheet (See FIG. 8). According to the caution, the user operates the bar code reader 5 within the input time limit. Since the operation of the bar code reader 5 is simple, the input can easily be accomplished within the time limit. When the input information is transmitted to the information receiving apparatus 1, the time required for input operation is transmitted together. This operation time information is acquired by utilizing, for example, a Cookie function.

The time limit determination section 86 in FIG. 9, determines, as stated above, whether or not the ID and password are input within the input time limit. If the ID and password are input within the time limit, the use of the bar code sheet distributed by the clinical result data administrator is considered. On the other hand, if the input time exceeded the time limit, there is a possibility that the keyboard is used.

Figure 10:
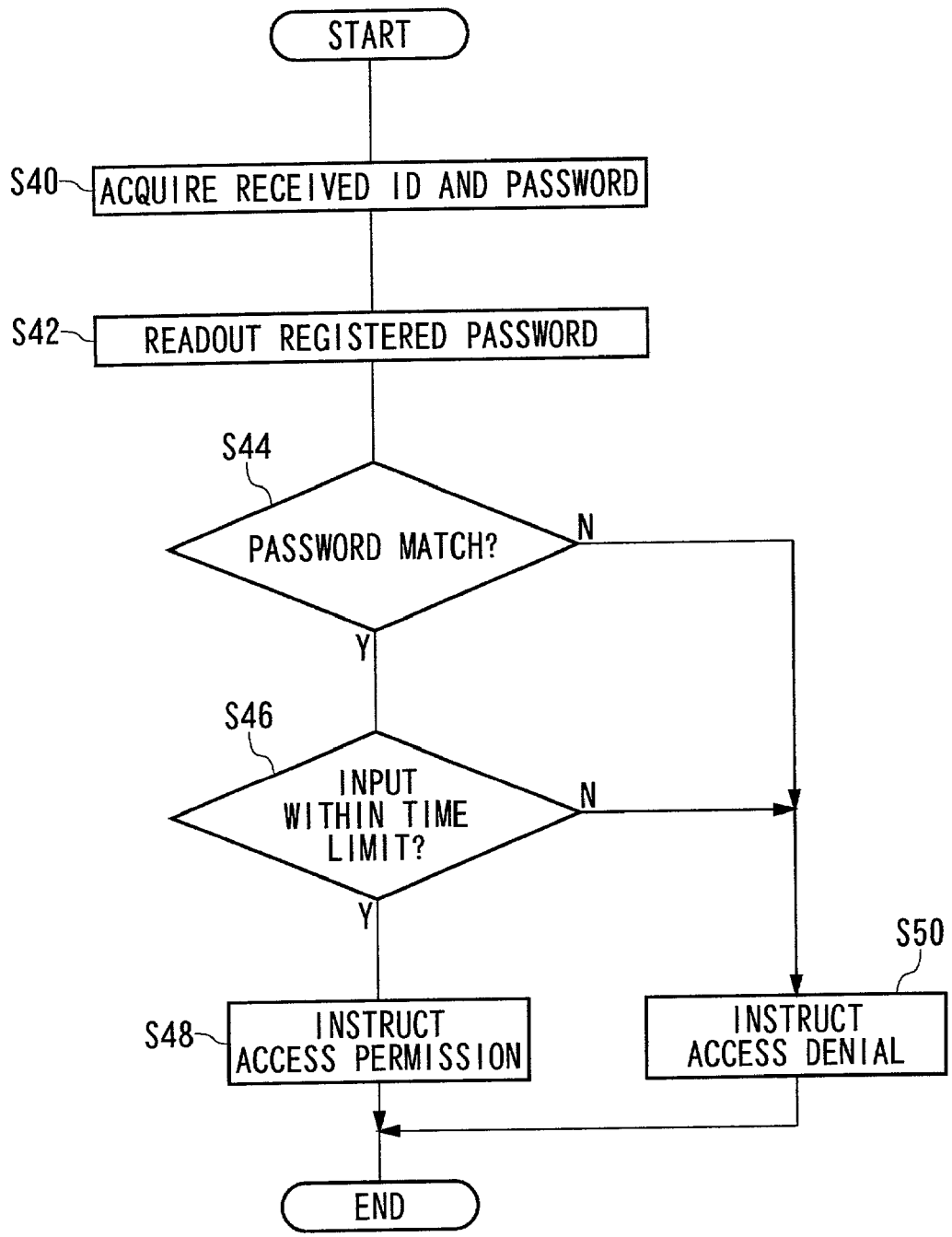
FIG. 10 shows the access permission process by the apparatus in FIG. 9.

FIG. 10 is a flow chart showing the process by the access permission device. Firstly, the ID and password sent from the information transmitting apparatus 3 are acquired (S40). Next, the password corresponding to the acquired ID is readout from the password memory section 82 (S42) and both passwords are matched (S44). If the passwords do not match, an access denial instruction is produced (S50). This includes a case of erroneous password, and a case of expiration of the valid term of the password.

If the passwords are matched in S44, the time limit determination section 86, determines whether or not the ID and password are input within the input time limit (S46). The access permission determination section 80 produces an instruction of access denial (S50) if S46 is NO, and produces an instruction of access permission (S48) if S46 is YES.

The access permission device and the access permission function are explained as above. Moreover, the ID and password are one of the access codes of the present invention. As variation examples, the time limit may only be set on the input of one of the ID and password. Alternatively, the ID and password are included in one bar code.

Also, the password memory section may memorize the information of the valid term in addition to the password. At the time of matching, in addition to the matching of the password, whether or not the present time is within the valid term may be determined.

A preferred embodiment of the present invention has been described above. The embodiment may, of course, be modified by those skilled in the art within the scope of the present invention.

For example, a readable code other than the bar code may be provided to the input sheet. The readable code is not limited to the code described (printed) on the sheet. For example, the readable code may be generated by an IC chip attached to the sheet. Also, in the case of using a reading device such as a pen type scanner capable of reading letters on the sheet, the readable code may be letters (including marks and numerical figures) described on the sheet. Also, the input sheet is typically paper, but can be other sheets, for example, a plastic sheet.

Also, in order to improve confidentiality, the information transmitting apparatus 3 is connected by an intermediate server other than the information receiving apparatus 1 via a telephone circuit (maybe a dedicated circuit) This intermediate server may be a WWW server held by an Internet provider. This intermediate server prepares an encrypted mail in which the information sent from the information transmitting apparatus 3 is written. This encrypted mail is sent to the information receiving apparatus 1 through the Internet. The information receiving apparatus 1 accumulates the information (test results) obtained by interpreting the mail in the database.

Further, the information receiving apparatus 1 may be connected to the information transmitting apparatus 3 directly by the telephone circuit (may be an exclusive circuit) without the Internet. In that case, the information may not go through the Internet. However, although the information does not go through the Internet, the Internet technology is preferably utilized. That is, similar to the above described embodiment, the information input page for Internet communication is sent to the information transmitting apparatus 3 by the telephone circuit. In response thereto, the information input by the user is sent to the information receiving apparatus 1. In this structure, the information receiving apparatus 1 is for the user terminal, in a position similar to the server of the provider to which the user is subscribed.

Advantageous points of the present invention will now be explained.

As stated above, the present invention utilizes the input sheet in input into the information input page for the Internet communication. The input sheet has input items to be established in the information input page, and also has the readable code, for example, the bar code to be input in the input item. The input work of the user may be to cause the reading device to read the code of the information to be input into the input item on the input sheet. The information read by the reading device is transmitted as the information to be input into the corresponding item on the information input page.

Therefore, the keyboard input operation by the user is reduced by the present invention. The user may input the information in each item of the input sheet by reading the code on the input sheet, and the input operation may be done in a sense similar to write—in by a pen to a conventional entry sheet. Further, if the reading device such as the bar code reader, etc. are used, the operation becomes simpler than when using a pen.

According to the above, with the present invention, the input operation into the information input page for the Internet communication is made much simple by the introduction of the input sheet. It is possible to make the input operation simple through the use of an input sheet while utilizing the conventional Internet technology.

Also, in the present invention, the explanation regarding the information to be input is described in the input sheet. The user sees the explanation of the input sheet and performs the input task on the input sheet. In this way, since the explanation of the information input page can be reduced, the design of the information input page may be simplified. The design of the system is further simplified.

Also, in the present invention, an access code, for example, the ID and password, is provided on the input sheet in the readable code. At the time of access, when the reading device reads the access code, the code is transmitted. The user may cause the reading device to read the access code. Therefore, the access task is simplified.

Also, in the present invention, the access code is an access code with a term limit on which the valid term is established. For example, the valid term is established on the password. When the access code is utilized within the valid term, the access is permitted. If the valid term is expired, the access code is renewed. The access code is used only within the valid term, so that, an unauthorized access may be effectively prevented.

Also, in the present invention, the input time limit of the access code is set according to the necessary time to input by using the reading device and at a time shorter than the minimum possible time to input the access code by the keyboard. In more detail, the input time limit is set greater than the standard time required for input operation using the reading device, and the access code is set at the length where the minimum time required for input operation using the keyboard is greater than the input time limit. When the access code is input within the input time limit, the access is permitted.

According to the present invention, depending on the length of time required for input of the access code, whether or not the reading device is used can be presumed. If more time is required than the input time limit, there is a possibility to use the keyboard. If the access code is input within the input time limit, it is considered that the reading device and input sheet are used. Access is permitted only in such a case. Therefore, unauthorized access may be effectively prevented.

Also, in the present invention, a numerical figure input area wherein readable codes to be used for input of numerical figures are arranged is provided. As shown in FIG. 7, in the numerical figure input area, the readable codes corresponding to the numerical figures are arranged in a matrix. The user can use the input sheet in the same sense as using a ten-key. Therefore, the input of numerical figures becomes easy.

Preferably, the readable code corresponding to the numerical figure is the multi dimension code. The multi dimension code is short compared with bar codes in ordinary strip design. Accordingly, as the matrix arrangement of readable codes can be made closer to the arrangement of normal ten-key, the input of numerical figures becomes easier.

Also, in the present invention, the input sheet has a plurality of input areas each having different input items, and a plurality of area specify codes respectively corresponding to the plural input areas. For example, in the above set of input sheets, each sheet is one input area. The information transmitting apparatus accepts input information to input areas corresponding to the area specify code read by the reading device. According to the present invention, the input sheet comprises a plurality of input areas, and a code specifying each input area is attached to the input sheet. When the area specify code is read, the information input to the applicable area is accepted. Therefore, in case of many input items, the input of each item can be reliably performed.

While there have been described what are at present considered to be preferred embodiments of the invention, it will be understood that various modifications may be made thereto, and it is intended that the appended claims cover all such modifications as fall within the true spirit and scope of the invention.

What is claimed is:

1. An information communicating system, comprising an information receiving apparatus and an information transmitting apparatus connected to said information receiving apparatus, said information transmitting apparatus being connected to a reading device which reads readable code from an input sheet, said input sheet having an input item to be established on an information input page for Internet communication as well as input information in a readable code to be input into said input item, said information transmitting apparatus transmitting the input information read from said input sheet by said reading device, as the input information into said information input page, to said information receiving apparatus;

wherein said input sheet has an access code in readable code necessary to access said information receiving apparatus from said information transmitting apparatus, and said information transmitting apparatus accesses said information receiving apparatus by transmitting to said information receiving apparatus the access code obtained from said input sheet by said reading device; and wherein an input time limit of said access code is set according to time necessary to input said access code by using said reading device, and shorter than the minimum input possible time to input said access code by keyboard, and when said access code is input within said input time limit, the access to said information receiving apparatus is permitted.

2. The information communicating system according to claim 1, wherein said access code is an access code with a term limit on which a prescribed valid term is established, and access to said information receiving apparatus is permitted when said information transmitting apparatus transmits said access code with said term limit read from said input sheet to said information receiving apparatus within said valid term.

3. The information communicating system according to claim 1, wherein a numerical figure input area, in which readable codes are arranged to be used for input of numerical figures, is provided on said input sheet, and the readable codes corresponding to numerical figures are arranged in a matrix in said numerical figure input area.

4. The information communicating system according to claim 3, wherein readable codes corresponding to numerical figures are multi dimension codes.

5. The information communicating system according to claim 1, wherein said input sheet has a plurality of input areas having different input items, and a plurality of area specify readable codes respectively corresponding to said plurality of input areas, and said transmission reception apparatus accepts input information corresponding to the area specify readable code read by said reading device.

6. An information transmitting apparatus which is connected to an information receiving apparatus and transmits input information to said information receiving apparatus, said information transmitting apparatus being connected to a reading device reading readable codes, said information transmitting apparatus transmitting, when said reading device reads input information from input sheet having an input item to be established on an information input page for Internet communication as well as input information in a readable code to be input into said input item, the read input information as input information into said information input page to said information receiving apparatus;

wherein a numerical figure input area, in which readable codes are arranged to be used for input of numerical figures, is provided on said input sheet, and readable codes corresponding to numerical figures are arranged in a matrix in said numerical figure input area and wherein said input sheet has a readable access code necessary to access said information receiving apparatus, and said information transmitting apparatus access said information receiving apparatus by transmitting to said information receiving apparatus the access code obtain from said input sheet by said reading device.

7. The information transmitting apparatus according to claim 6, wherein the readable codes corresponding to the numerical figures are multi dimension codes.

8. The information transmitting apparatus according to claim 6, wherein said input sheet has a plurality of input areas having different input items, and a plurality of area specify readable codes respectively corresponding to said plurality of input areas, and said information transmitting apparatus accepts input information corresponding to the area specify readable code read by said reading device.

9. An information transmitting method for transmitting information from an information transmitting apparatus to an information receiving apparatus, said method transmitting, when input information is read by a reading device reading a readable code from an input sheet having input items established on an information input page for Internet communication as well as input information to be input into said input items in readable code, the read input information to said information receiving apparatus as input information to said information input page;

wherein when an area specify code is read by said reading device from an input sheet having a plurality of input areas each of which has different input items and a plurality of area specify readable codes respectively corresponding to said plural input areas, said method accepts input information to the input area corresponding to the read area specify readable code wherein said reading device reads an access code necessary to access said information receiving apparatus from said input sheet, said method accesses said information receiving apparatus by transmitting the access code from said information transmitting apparatus to said information receiving apparatus.

* * * * *

UNITED STATES PATENT AND TRADEMARK OFFICE
CERTIFICATE OF CORRECTION

PATENT NO. : 7,162,527 B2
APPLICATION NO. : 10/194299
DATED : January 9, 2007
INVENTOR(S) : Kiko Tanaka et al.

It is certified that error appears in the above-identified patent and that said Letters Patent is hereby corrected as shown below:

In claim 6, column 12, line 46, "apparatus which" should read --apparatus, which--.

In claim 6, column 12, line 63, "input area and" should read --input area; and--.

In claim 6, column 12, Line 66, "access" should read --accesses--.

In claim 6, column 13, line 2, "obtain" should read --obtained--.

In claim 9, column 14, line 10, "readable code wherein said" should read --readable code; and wherein, when said--.

Signed and Sealed this

Sixth Day of November, 2007

JON W. DUDAS
*Director of the United States Patent and Trademark Office*